United States Patent [19]

Davis et al.

[11] Patent Number: 4,540,566

[45] Date of Patent: Sep. 10, 1985

[54] PROLONGED RELEASE DRUG DOSAGE FORMS BASED ON MODIFIED LOW VISCOSITY GRADE HYDROXYPROPYLMETHYLCELLULOSE

[75] Inventors: Stanley S. Davis, Nottingham, England; Norman G. Gaylord, New Providence, N.J.

[73] Assignee: Forest Laboratories, Inc., New York, N.Y.

[21] Appl. No.: 596,095

[22] Filed: Apr. 2, 1984

[51] Int. Cl.³ .......................... A61K 9/22; A61K 9/26
[52] U.S. Cl. ........................................ 424/22; 424/19; 424/35; 514/781; 514/964
[58] Field of Search .................... 424/19–22, 424/35, 362

[56] References Cited

U.S. PATENT DOCUMENTS

| | | | |
|---|---|---|---|
| 3,065,143 | 11/1962 | Christenson et al. | 424/19 |
| 3,870,790 | 3/1975 | Lowey et al. | 424/362 |
| 4,226,849 | 10/1980 | Schor | 424/19 |
| 4,259,314 | 3/1981 | Lowey | 424/19 |
| 4,264,573 | 4/1981 | Powell et al. | 424/19 |
| 4,344,934 | 8/1982 | Martin et al. | 424/80 |
| 4,369,172 | 1/1983 | Schor et al. | 424/19 |
| 4,389,393 | 6/1983 | Schor et al. | 424/19 |

FOREIGN PATENT DOCUMENTS

| | | |
|---|---|---|
| 12523 | 6/1980 | European Pat. Off. . |
| 2732335 | 2/1978 | Fed. Rep. of Germany . |
| 2021143 | 11/1979 | United Kingdom . |
| 2098867 | 12/1982 | United Kingdom . |

OTHER PUBLICATIONS

Daly et al, Int. J. Pharm., 18(1–2):201–205 (1984) The Effect of Anionic Surfactants on the Release of Chlorpheniramine Maleate from a Polymer Matrix Tablet.
Krycer et al., Powder Technol., 34(1):39–50 (1983) An Evaluation of Tablet Binding Agents.

*Primary Examiner*—Shep K. Rose
*Attorney, Agent, or Firm*—Jacobs & Jacobs

[57] ABSTRACT

A carrier base material combined with a therapeutically active medicament and shaped and compressed to a solid unit dosage form having a controlled and prolonged release pattern upon administration, the carrier base material being a mixture of one or more nonionic cellulose ethers and an anionic surfactant, and wherein at least one of the cellulose ethers is a modified hydroxypropylmethylcellulose having a number average molecular weight of less than 50,000 and has been modified by successive or concurrent exposure to moisture and air.

9 Claims, No Drawings

PROLONGED RELEASE DRUG DOSAGE FORMS BASED ON MODIFIED LOW VISCOSITY GRADE HYDROXYPROPYLMETHYLCELLULOSE

BACKGROUND OF THE INVENTION

1. Field of Invention

This invention relates to a carrier base material to be combined with a therapeutically active medicament and formed into a solid, shaped unit dosage form having a controlled and prolonged incremental release of the medicament upon administration. Specifically, this invention relates to a mixture of a modified nonionic cellulose ether and an anionic surface active agent which is suitable for use in controlled release therapeutic compositions.

2. Description of the Prior Art

Water-soluble nonionic cellulose ethers have been used as binders, matrices or carrier bases in sustained release solid dosage forms containing active medicaments, accompanied by lubricants and excipient fillers, as needed. Methylcellulose and hydroxypropylmethylcellulose, particularly the latter, are among the nonionic cellulose ethers which have been most widely used in this manner.

The cellulose ethers are commercially available in various grades under several trade names. The grades available under a given trade name represent differences in composition and molecular weight. Thus, water-soluble methylcellulose (Methocel A, previously designated as Methocel MC, from The Dow Chemical Co., U.S.A. and Metolose SM from Shin-Etsu, Ltd., Japan) has a methoxyl content of 27.5–31.5 weight-% and is available in various viscosity grades. Hydroxypropylmethylcellulose is actually a series of compounds (Methocel E, F, J and K, all previously designated as versions of Methocel HG, from The Dow Chemical Co., U.S.A., and Metolose SH from Shin-Etsu, Ltd., Japan), each of which has a different chemical composition with a methoxyl content within the range of 16.5 to 30 weight-%, a hydroxypropyl content within the range of 4 to 32 weight-% and each of which is available in various viscosity grades.

Commercial designations of the various cellulose ethers are based on the viscosities of 2% aqueous solutions at 20° C. The viscosities range from 5 cps to 100,000 cps and represent number average molecular weights ranging from below 10,000 to over 150,000, as calculated from the data in "Handbook of Methocel Cellulose Ether Products" (The Dow Chemical Co., 1974).

Christenson and Dale (U.S. Pat. No. 3,065,143) and Huber, Dale and Christenson (J. Pharm. Sci., 55, 974 (1966) disclosed the preparation of a sustained release drug tablet wherein a high viscosity grade, i.e. high molecular weight, hydroxypropylmethylcellulose, was present as binder to the extent of at least one third of the weight of the tablet. The binders included 4000 cps viscosity grade Methocel 60HG, now known as Methocel E4M, having a 28–30 weight-% methoxyl content, a 7.5–12 weight-% hydroxypropoxyl content and a number average molecular weight of 93,000, as well as 4000 cps and 15,000 cps viscosity grades Methocel 90HG, now known as Methocel K4M and Methocel K15M, respectively, having a 19–24 weight-% methoxyl content, a 4–12 weight-% hydroxypropoxyl content and number average molecular weights of 89,000 and 124,000, respectively.

Christenson and coworkers proposed that water was rapidly absorbed and formed a gel barrier on the surface of the tablet. Drug release was controlled by drug diffusion from and attrition of the gel barrier.

Christenson and Huber (U.S. Pat. No. 3,590,117) reported that neither low viscosity grade hydroxypropylmethylcellulose nor high viscosity grade, i.e. 15,000 cps, hydroxypropylmethylcellulose made acceptable long-lasting troches.

Lapidus (Dissertation, Rutgers State University, 1967) and Lapidus and Lordi (J. Pharm. Sci., 55, 840 (1966); 57, 1292 (1968) studied the use of high viscosity grade methylcellulose (4000 cps viscosity grade Methocel MC now designated as Methocel A4M) and/or low and high viscosity grade hydroxypropylmethylcellulose (25 cps and 15,000 cps viscosity grade Methocel 90HG now designated as Methocel K25 and Methocel K15M, respectively) in compressed pharmaceutical tablets and confirmed the proposal of Christenson et al. that drug diffusion and attrition of the hydrated layer determined the rate of drug release.

Salomon, Doelker and Buri (Pharm. Acta Helv., 54 (3), 82 (1979) disclosed the use of 15,000 cps viscosity grade Methocel 90HG (now designated as Methocel K15M) in a tablet containing potassium chloride.

Sheth and Tossounian (U.S. Pat. Nos. 4,126,672; 4,140,755; 4,167,558) disclosed solid dosage forms containing 4000 cps viscosity grade methylcellulose or hydroxypropylmethylcellulose in combination with various additives including gas-generating compounds, e.g. calcium carbonate, and inert fatty materials, so as to by hydrodynamically balanced so that they have a bulk density of less than one in contact with gastric fluid.

Schor, Nigalaye and Gaylord (U.S. Pat. No. 4,389,393) disclosed sustained release solid unit dosage forms in which the carrier base material constituted less than one third of the weight of the dosage form and consisted of hydroxypropylmethylcellulose of at least 4000 cps viscosity grade, having a methoxyl content of 16–24 weight-%, a hydroxypropyl content of 4–32 weight-% and a number average molecular weight of at least 50,000, i.e. Methocel J and Methocel K or Metolose 90SH.

The use of high viscosity grades of methylcellulose Methocel A and hydroxypropylmethylcellulose Methocel E, Methocel F and Methocel K, in sustained release solid drug dosage forms is also described in a technical bulletin "Formulating Sustained Release Pharmaceutical Products with Methocel" (The Dow Chemical Co., 1982).

The cited prior art discloses that high viscosity grades of hydroxypropylmethylcellulose of various chemical compositions are useful in the preparation of sustained release solid drug dosage forms. However, Schor, Nigalaye and Gaylord (U.S. Pat. No. 4,369,172) disclosed that effective prolonged release therapeutic compositions were prepared by using as a carrier base material, a low viscosity grade hydroxypropylmethylcellulose having a hydroxypropoxyl content of 9–12 weight-% and a number average molecular weight of less than 50,000.

Lowey and Stafford (U.S. Pat. No. 3,870,790) and Schor (U.S. Pat. No. 4,226,849) disclosed that effective sustained release tablets were produced by using as carrier base material, a modified low viscosity grade hydroxypropylmethylcellulose having a hydroxypropoxyl content of less than 9 weight-% and a number average molecular weight of 23,000, e.g. Methocel E50. The modification was carried out by exposure of the low molecular weight hydroxypropylmethylcellulose to high humidity or moisture and drying in air, resulting in an increase in the carboxyl content of the polymer.

Lowey (U.S. Pat. No. 4,259,314) disclosed the use of a mixture of hydroxypropylmethylcellulose having a viscosity in the range of 50 to 4000 cps, and hydroxypropylcellulose in the preparation of a controlled release pharmaceutical composition.

The present invention is directed toward further improvements in carrier base materials containing nonionic cellulose ethers for use in the preparation of prolonged release solid pharmaceutical unit dosage forms. These improvements result from the presence of an anionic surfactant.

The addition of 1% of some anionic salts of alkyl sulfates, alkyl sulfonates or alkylaryl sulfonates to 1% aqueous solutions of methylcellulose (Methocel A) or hydroxypropylmethylcelluloses (Methocel E, Methocel F and Methocel K) results in an increase in the viscosity of the cellulose ether solution ("Handbook on Methocel Cellulose Ether Products", The Dow Chemical Co., 1975).

An increase in the rate of solution of a drug results from the presence of anionic surfactants, such as dioctyl sodium sulfosuccinate and/or sodium lauryl sulfate, in the dissolution medium or incorporated into compressed drug tablets, containing water-insoluble binders, including polyethylene (Desai et al., J. Pharm Sci., 54, 1459 (1965); 55, 1224, 1230 (1966), polyvinyl chloride (Desai et al., J. Pharm. Sci., 55, 1235 (1966) and wax (Dakkuri et al., J. Pharm. Sci., 67, 354 (1978); Chambliss, J. Pharm. Sci., 70, 1248 (1981). The presence of sodium lauryl sulfate in a quinine sulfate tablet containing a polyamide binder, decreased the rate of solution of the drug at ph 1.5 but had little effect at pH 7.5 (Choulis et al., Pharmazie, 30, 233 (1975).

SUMMARY OF THE INVENTION

An object of the present invention is to provide a carrier base material for use in the preparation of orally, bucally, sublingually, etc., administered lozenges and tablets, as well as suppositories and other solid unit dosage forms which have a controlled and prolonged release pattern for a systemically absorbable medicament or active ingredient incorporated therein.

Another object of the present invention is to provide a carrier base material having a more prolonged release pattern of the active medicament from a low viscosity grade nonionic cellulose ether.

It has now been found that these improvements in a carrier base material can be achieved by admixture of an anionic surfactant and a modified low viscosity grade hydroxypropylmethylcellulose.

DETAILED DESCRIPTION OF THE INVENTION

According to the present invention, it has now been found that important advantages and improvements over prior art products containing water-soluble nonionic cellulose ethers as carrier base materials can be obtained by admixture of an anionic surfactant with a modified low viscosity grade nonionic cellulose ether, specifically hydroxypropylmethylcellulose. This is particularly surprising since it has been disclosed in our co-pending application Ser. No. 592,570 filed Mar. 26, 1984 that similar improvements can be obtained by admixture of an anionic surfactant with a high viscosity grade methylcellulose or hydroxypropylmethylcellulose.

The modified low viscosity grade hydroxypropylmethylcellulose which is effective in the present invention is prepared as described in U.S. Pat. Nos. 3,870,790 and 4,226,849. A 50 cps viscosity grade hydroxypropylmethylcellulose having a methoxyl content of 28–30 weight-%, a hydroxypropoxyl content of 7.5–12 weight-% and a number average molecular weight of 23,000, e.g. Methocel E50 from The Dow Chemical Co., U.S.A., or Metolose 60SH50 from Shin Etsu Ltd., Japan, is subjected to sucessive or concurrent hydrolysis and oxidation.

In the successive treatment, hydrolysis of the nonionic cellulose ether is carried out either by humidification of the cellulose ether in a chamber at ambient or elevated temperature until the humidity of the chamber reaches at least 85% and the humidity is maintained for at least 12 hours or by mixing the cellulose ether with water and heating to a temperature of 30°–100° C. for at least 12 hours. Oxidation is carried out at 30° to 50° C. in the presence of oxygen or a stream of air. Concurrent hydrolysis and oxidation is carried out by treatment of the cellulose ether with air or oxygen containing a sufficient amount of water at an elevated temperature.

The anionic surfactants which are effective in the present invention include alkali metal sulfates of linear and branched alcohols, ethoxylated alcohols, ethoxylated alkylphenols, ethoxylated acids, ethoxylated amides, oils, fatty esters, etc., alkali metal salts of sulfonates of naphthalene, alkylnaphthalenes, naphthalene condensates, alkyl-substituted benzenes, diphenyl derivatives, α-olefins, petroleum, oils, fatty acids, etc., as well as the alkali metal salts of dialkyl sulfosuccinates.

Representative anionic surfactants include sodium or potassium dodecyl sulfate, sodium octadecyl sulfate, sodium sulfated castor oil, sodium dodecylbenzene sulfonate, sodium linear alkylate sulfonate, sodium sulfonated mineral oil, sodium petroleum sulfonate, sodium salt of naphthalenesulfonic acid-formaldehyde condensate, dioctyl sodium sulfosuccinate and the like.

The weight ratio of anionic surfactant to modified low viscosity grade hydroxypropylmethylcellulose in the solid dosage forms may be 0.005/1 to 3/1. The solid dosage forms may contain from 5 to 95 weight-% of the modified nonionic cellulose ether.

The modified cellulose ether of the present invention in admixture with the anionic surfactant and an active medicament has excellent compressibility and the tablets prepared therefrom are hard and dense, have low friability and provide controlled and prolonged release over an extended period.

Solid drug forms containing the mixture of anionic surfactant and modified hydroxypropylmethylcellulose of the present invention are stable and the release rate does not change over an extended storage period.

The modified cellulose ether can be used as the sole cellulose ether, in admixture with an anionic surfactant, in the carrier base material or can be used in admixture with other nonionic cellulose ethers having the same or different structure, with a higher molecular weight, or with sodium carboxymethylcellulose.

The active ingredient can be of any type of medication which acts locally in the mouth or systemically, which in the case of the latter, can be administered orally to transmit the active medicament into the gas- -continued

| Ingredients | Example No. | |
|---|---|---|
| | 1 mg/tablet | 5–6 mg/tablet |
| 2. Modified hydroxypropylmethyl-cellulose | 255 | 210 |
| 3. Sodium alkyl sulfate | 0 | 45 |

Ingredients 1, 2 and 3 were blended in a V-blender rotating at 30 rpm for 45 minutes. The total batch weight was sufficient for 250 tablets. The mixture was compressed on a Manesty F3 single punch tablet machine fitted with a 10 mm diameter flatfaced punch and die.

The release rate was determined using the rotating basket dissolution apparatus described in USP XX, page 959 with a rotation speed of 100 rpm. The dissolution medium was 0.1N HCl and was maintained at 37° C.

The 45 mg chlorpheniramine maleate tablets had the following properties:

| Example No. | Sodium alkyl sulfate | Dissolution, % | | |
|---|---|---|---|---|
| | | 25 | 50 | 75 |
| | | Dissolution time, hours | | |
| 1 | None | 0.5 | 1.7 | 3.6 |
| 2 | Sodium octyl sulfate | 2.7 | >6 | — |
| 3 | Sodium decyl sulfate | 1.9 | 4.0 | 6.0 |
| 4 | Sodium dodecyl sulfate | 1.5 | 3.9 | 6.0 |
| 5 | Sodium hexadecyl sulfate | 1.2 | 3.9 | >6 |
| 6 | Sodium octdecyl sulfate | 0.9 | 3.4 | >6 |

EXAMPLES 7–8

Chlorpheniramine maleate tablets were prepared using the modified hydroxypropylmethylcellulose in the same manner as in Examples 1–6. The tablets were prepared in the absence and in the presence of dioctyl sodium sulfosuccinate (DSS granular—U.S.P. containing 85% DSS and 15% sodium benzoate).

The 45 mg chlorpheniramine maleate tablets were prepared from the following ingredients:

| Ingredients | Example No. | |
|---|---|---|
| | 7 mg/tablet | 8 mg/tablet |
| 1. Chlorpheniramine maleate | 45 | 45 |
| 2. Modified hydroxypropylmethyl-cellulose | 263 | 210 |
| 3. Dioctyl sodium sulfosuccinate (DSS granular - USP) | 0 | 53 |

The tablets were prepared in the same manner as described in Examples 1–6 and the release rate was determined in 0.1N HCl at 37° C. as described in Examples 1–6.

The 45 mg chlorpheniramine maleate tablets had the following properties:

| | Example No. | |
|---|---|---|
| | 7 | 8 |
| DSS | Absent | Present |
| Weight, mg | 308 | 308 |
| Dissolution, % | Time, hours | |
| 25 | 0.5 | 0.7 |
| 50 | 1.7 | 4.0 |
| 75 | 3.6 | 7.0 |

EXAMPLES 9–12

Sodium salicylate tablets were prepared using the modified hydroxypropylmethylcellulose in the same manner as in Examples 1–6. The tablets were prepared in the absence and in the presence of various sodium alkyl sulfates.

The 45 mg sodium salicylate tablets were prepared from the following ingredients:

| Ingredients | Example No. | |
|---|---|---|
| | 9 mg/tablet | 10–12 mg/tablet |
| 1. Sodium salicylate | 45 | 45 |
| 2. Modified hydroxypropylmethyl-cellulose | 255 | 210 |
| 3. Sodium alkyl sulfate | 0 | 45 |

The tablets were prepared in the same manner as described in Examples 1–6 and the release rate was determined in 0.1N HCl at 37° C. as described in Examples 1–6.

The 45 mg sodium salicylate tablets had the following properties:

| Example No. | Sodium alkyl sulfate | Dissolution, % | | |
|---|---|---|---|---|
| | | 25 | 50 | 75 |
| | | Dissolution time, hours | | |
| 9 | None | 1.2 | 3.0 | 4.8 |
| 10 | Sodium octyl sulfate | 1.5 | 3.4 | 5.9 |
| 11 | Sodium decyl sulfate | 1.8 | 4.4 | 7.0 |
| 12 | Sodium dodecyl sulfate | 1.9 | >6 | — |

The foregoing is exemplary and illustrative of compositions and products responding to the present invention, but it is to be understood that they are not limitative since many active medicaments of various types can be employed in the new controlled and long-lasting carrier so long as they are absorbable into blood or tissue from the general intestinal tract and other bodily surfaces and areas. The medicaments shown in our U.S. Pat. No. 4,369,172 may be used in the practice of the present invention and are incorporated herein by reference. The invention is also intended to cover other dosage forms or forms for application of controlled release ingredients such as vaginal and rectal suppositories and buccal tablets. Lozenges and compressed tablets particularly act on oral, oropharyngeal, pharyngeal and intestinal regions. The total dosage is governed by usual medical considerations or physician's directions and when sufficiently large doses of active medicament are incorporated into the unit dosage form, systemic as well as local action is obtained to overcome or control the pathological condition or disorder being treated.

What is claimed is:

1. A carrier base material combined with a therapeutically active medicament and shaped and compressed to a solid unit dosage form having a controlled and prolonged release pattern upon administration, the carrier base material being a mixture of one or more water-soluble nonionic cellulose ethers and an anionic surfactant, and wherein at least one of the cellulose ethers is a modified hydroxypropylmethylcellulose having a number average molecular weight of less than 50,000 and has been modified by successive or concurrent exposure to moisture and air.

trointestinal tract and into the blood, fluids and tissues of the body without excessive peak concentrations occurring. Alternatively, the active ingredient can be of any type of medication which acts through the buccal tissues of the mouth to transmit the active ingredient directly into the blood stream thus avoiding first pass liver metabolism and by-passing the gastric and intestinal fluids which have an adverse inactivating or destructive action on many active ingredients unless they are especially protected against such fluids as by means of an enteric coating or the like. The active medicament can also be of a type of medication which can be transmitted into the blood circulation through the rectal tissues. Thus, the invention is applicable to sublingual lozenges, buccal tablets, suppositories and compressed tablets. The latter are intended to be swallowed in unit dosage form and upon ingestion according to a prescribed regimen give controlled and slow release of the active medicament, while being protected against inactivating gastric fluids.

Representative active medicaments include antacids, anti-inflammatory substances, coronary vasodilators, cerebral vasodilators, peripheral vasodilators, anti-infectives, psychotropics, antimanics, stimulants, antihistamines, laxatives, decongestants, vitamins, gastrointestinal sedatives, antidiarrheal preparations, antianginal drugs, antiarrythmics, anti-hypertensive drugs, vasoconstrictors and migraine treatments, anticoagulants and antithrombotic drugs, analgesics, anti-pyretics, hypnotics, sedatives, antiemetics, antinauseants, anticonvulsants, neuromuscular drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, antiuricemic drugs and other drugs or substances acting locally in the mouth, such as topical analgesics, local anaesthetics, etc.

The mixture of anionic surfactant and modified low viscosity grade hydroxypropylmethylcellulose forms what is called a long-acting, slow dissolving carrier of such a nature that it has a protective, demulcent and buffering effect in the body and causes the active medicament to exert its optimum therapeutic action immediately and incrementally for an extended period of time, so that full therapeutic advantage can be taken of the entire or substantially the entire amount of active medicament administered. This unexpectedly high degree of efficiency is a particular advantage of the invention and minimizes the side effects of the medication.

In making up tablets containing an orally administrable systemically absorbable active component such as one of the heretofore mentioned medicaments, the modified cellulose ether and the anionic surfactant are thoroughly intermixed with the medicament which is in powdered or granular form or in solution, and any other needed ingredients which are conventional in tablet making such as magnesium stearate, stearic acid, lactose, starch, fumed silica, hydrogenated vegetable oil and, in general, binders, fillers, disintegrating agents and the like. The modifed cellulose ether and the surfactant may be mixed in water, alcohol or other media known in the art, and dried to produce granules before intermixing with the medicament and other ingredients. Alternatively, the medicament may be granulated with the modified cellulose ether and surfactant before intermixing with the other ingredients.

The complete mixture, in an amount sufficient to make a uniform batch of tablets, e.g. 50,000, of which each contains an effective amount of active medicament, is then subjected to tabletting in conventional tabletting machines at compression pressures of 140 to 1125 kg/sq. cm., and because of the use of the specific carrier material of this invention in the production of the tablets, a product is obtained which has the desired hardness, low level of friability and a predetermined controlled and prolonged action and a regular delayed release pattern so that the medicament is available over a period of 0.25–36 hours, depending upon the precise tablet size, hardness and the particular carrier composition. In this way, it is possible to produce controlled and slow continuous release tablets in relatively simple and economical manner on a commercial scale as contrasted with the more elaborate and more complex materials and procedures heretofore employed or proposed.

The moisture content of the carrier used in the preparation of the controlled release tablets may be in the 0.1–10% range, the lower end of the range being preferable when moisture sensitive medicaments are used. If the moisture content is outside of this range, it may be brought within the range by the use of ambient or hot, dry or wet air, using appropriate equipment including static, convection, forced air or vacuum chambers or other equipment well known to those skilled in the art. The moisture content of the carrier during tabletting influences the integrity of the tablet obtained under a given compression pressure. However, the moisture content has less influence on the prolonged release characteristics than the composition of the carrier and its concentration.

The release pattern of active medicament from the carrier of the present invention can be controlled according to the particular medication and its intended therapeutic effect. For a sublingual lozenge or tablet, the release pattern may be varied from about 15 minutes to 4 hours. For orally administered tablets, the release time may be 2–4 hours, 4–8 hours, 8–14 10 hours, 10–12 hours, 15–18 hours, 20–24 hours, etc., as desired. For buccal tablets, the release period may be 15 minutes to 24 hours. For vaginal and rectal suppositories, the release pattern ranges from 2 to 36 hours and can be more or less where indicated. Predetermined release patterns of unusually reliable characteristics can be secured. The invention is of very versatile and adaptable nature giving it a wide range of application and end use.

The following illustrative embodiments of the disclosures of the present invention are non-limiting and variations will be obvious to those skilled in the art.

EXAMPLES 1–6

Chlorpheniramine maleate tablets were prepared using a modified hydroxypropylmethylcellulose ("Synchron"), prepared from Methocel E50 by exposure to moisture or high humidity at elevated temperature, followed by drying in air, as described in U.S. Pat. No. 4,226,849. The tablets were prepared in the absence and in the presence of various sodium alkyl sulfates.

The 45 mg chlorpheniramine maleate tablets were prepared from the following ingredients:

| | Example No. | |
|---|---|---|
| Ingredients | 1 mg/tablet | 5–6 mg/tablet |
| 1. Chlorpheniramine maleate | 45 | 45 |

2. A composition according to claim 1 wherein the hydroxypropylmethylcellulose has a methoxyl content of 28–30 weight-% and a hydroxypropoxyl content of 7.5–12 weight-%.

3. A composition according to claim 1 wherein the anionic surfactant is an alkali metal salt of an organic sulfate.

4. A composition according to claim 3 wherein the organic sulfate is selected from the group consisting of $C_8$–$C_{24}$ alcohol sulfates.

5. A composition according to claim 3 wherein the organic sulfate is the sulfate of an ethoxylated compound.

6. A composition according to claim 1 wherein the anionic surfactant is an alkali metal salt of an organic sulfonate.

7. A composition according to claim 6 wherein the organic sulfonate is an aryl sulfonate.

8. A composition according to claim 6 wherein the organic sulfonate is a dialkyl sulfosuccinate.

9. A method for the preparation of a therapeutically active solid unit dosage form having a controlled and prolonged release pattern upon administration, consisting of compressing and shaping a mixture of a therapeutically active medicament and a carrier base material consisting of a mixture of one or more water-soluble nonionic cellulose ethers and an anionic surfactant, and wherein at least one of the cellulose ethers is a modified hydroxypropylmethylcellulose having a number average molecular weight of less that 50,000 and has been modified by successive or concurrent exposure to moisture and air.

* * * * *